(12) United States Patent
Siebel

(10) Patent No.: US 7,364,590 B2
(45) Date of Patent: Apr. 29, 2008

(54) ANATOMICAL KNEE PROSTHESIS

(76) Inventor: Thomas Siebel, Ritterweg 3, D-66130 Saarbrücken (DE)

( * ) Notice: Subject to any disclaimer, the term of this patent is extended or adjusted under 35 U.S.C. 154(b) by 0 days.

(21) Appl. No.: 10/409,356

(22) Filed: Apr. 8, 2003

(65) Prior Publication Data
US 2004/0204766 A1 Oct. 14, 2004

(51) Int. Cl.
*A61F 2/38* (2006.01)
(52) U.S. Cl. .................................................. 623/20.35
(58) Field of Classification Search ... 623/20.14–20.36
See application file for complete search history.

(56) References Cited

U.S. PATENT DOCUMENTS

| RE29,757 E | * | 9/1978 | Helfet | 623/20.31 |
| 4,711,639 A | * | 12/1987 | Grundei | 623/20.33 |
| 5,194,066 A | * | 3/1993 | Van Zile | 623/20.15 |
| 5,824,105 A | * | 10/1998 | Ries et al. | 623/20.31 |

* cited by examiner

Primary Examiner—Alvin J. Stewart
(74) Attorney, Agent, or Firm—Friedrich Kueffner

(57) ABSTRACT

An anatomical knee prosthesis configured to be oriented on an anatomical line of an interarticular space of the knee and not oriented on a mechanical axis as far as the interarticular space of the knee is concerned.

19 Claims, 8 Drawing Sheets (a)

(b)

(a)

(b)

(a)

(b)

ANATOMICAL KNEE PROSTHESIS

BACKGROUND OF THE INVENTION

According to FIG. 1, previous knee prosthesis are oriented on the so-called mechanical axis $\delta_1$ with respect to its joint line 2'. The mechanical axis $\delta_1$ is the line that runs vertically from the center 1 of the head of the femur through the knee joint 3 to the ankle 4. The joint lines 2' and 5' of previous knee prosthesis implants were implanted at an angle of ($\beta_1$) 90° to this mechanical axis. The medial and lateral condyles of the femur were equally large in regard to their polycentric radius.

In reality, it is now the case that the joint line 5 of the upper ankle joint 4 to the axis $\delta_1$ forms an angle ($\alpha_1$) of 85°±5° ascending medially and descending laterally. Furthermore, in the region of the knee joint line 2, the anatomical healthy knee joint also does not form a right angle with the mechanical axis $\delta_1$ that was assumed at that time, but rather the tibial plateau descends medially by an angle ($\beta_2$) of about 3°±x or ascends laterally by 3°±x relative to the mechanical axis $\delta_1$. The consequence of this is that the condyles of the femur have different radii. Laterally, the polycentric radii are somewhat smaller in the side view, while the medial condyle of the femur is distinctively larger with polycentric radii, as far as the radial diameter is concerned. The bearing surface in the a.p. plane is somewhat narrower in the case of the medial condyle of the femur, compared to the lateral condylar part. In addition, it should be noted that the tibial plateau drops by 3-7° in the dorsal direction.

Now, since the knee joint carries out an internal rotation in the course of knee flexion, the medial part of the femoral condylar structure moves ventrally (uphill, so to speak, with respect to the tibial plateau), whereas the lateral part of the condylar structure of the femur moves dorsally and thus downhill, so to speak. The 3° axis in the knee joint (towards the old mechanical axis $\delta_1$), which is already present anyway, is thus indirectly enlarged, so that the tibial plateau no longer forms an angle of 3° with the original old mechanical axis $\delta_1$, but rather now forms an angle of 3°+x, which then corresponds approximately to the angle of the upper ankle joint in relation to the former mechanical axis, i.e., generally about 5°.

Of course, independently of this, these polycentric radii also have an effect on the point of attachment of the collateral ligaments, which must be continually under tension, such that by changing the anatomical conditions by creating two equally large femoral condyles and a horizontal tibial plateau, conditions that differ completely from the anatomy are created here for the collateral ligaments as well. For this reason, the further inventive step of developing an anatomical knee prosthesis is taken here, which is intended to take these anatomical conditions exactly into account. All of the problems are solved by the features specified in the claims.

SUMMARY OF THE INVENTION

The essential features of this knee prosthesis include, first, the femoral condyles with differently pronounced polycentric condylar parts, such that the medial condylar part has a larger polycentric radius than the lateral part, so that an angle of about 3° to the mechanical axis (old mechanical axis $\delta_1$) is achieved here, which means, assuming that a femoral medullary space stem is to be fixed to the implant, that this must have an angle of about 10° to the shaft and not, as in the old prostheses, an angle $\gamma$ of 7°. As in the anatomical specimen, the medial part of the condyle of the femur may be narrower in its bearing surface than the lateral part of the condyle of the femur. Optionally, the femoral condylar components may also be individually assembled medially and laterally as units in the sense of a unicondylar sliding prosthesis, in which case a patellar shield may also be optionally added in the front. The tibial plateau must be anatomically implanted, i.e., descending dorsally by 3-7°, descending medially by about 3°, and, with respect to the bearing surface, more pronounced medially than laterally. To be able to produce the medially descending angle of 3°, the tibial plateau can then be provided with a stem, which forms an angle of 87° in the medial direction, or which, with a stem fixed at right angles on the tibial plateau implant, is inserted in the bone only at a medially descending angle of 3°±x.

Alternatively, a different polyethylene inlay level should be set on the tibial plateau metal implant with the stem fixed at right angles, so that an angle which is truer to the anatomical situation is produced by the polyethylene inlay part, which is somewhat deeper medially than laterally.

Alternatively, a rotating polyethylene monoblock with different medial and lateral levels is then also conceivable and possible. Furthermore, the tibial plateau may also be implanted as so-called unicondylar medial and lateral implants to reconstruct the anatomical downward slope in the medial and dorsal direction.

The polyethylene components must be individually insertable medially and laterally, so that the joint line, as seen from the front, i.e., from medial to lateral, is reproduced. In addition, the polyethylene inlays should have different dorsal slopes, so that in the case of a metallic tibial plateau component horizontally mounted in the lateral plane, the dorsal slope (tibial slope), which is usually different medially and laterally, is optimally reproduced.

Finally, a tibial implant variant is possible by means of a stepped resection of the tibial joint surface (medial lower than lateral) and introduction of a tibial implant with corresponding bearing surface with different height levels, which makes it possible to create a medially downward sloping tibial joint surface, with the introduction of force directed at an angle of 90° to the shaft of the tibia.

Finally, the overall effect of the present form of the knee prosthesis is to reproduce the anatomy of the healthy knee joint. As a result of the altered design of the condyles of the femur and the altered course of the joint line from earlier endoprosthetic implants, which were based on the false notion that the mechanical axis $\delta_1$ is vertical to the talus, which does not conform to the facts, optimized knee joint kinematics are present, since the ligament stresses remain largely identical as a result of the unchanged anatomy, so that less stress is placed on the implant-bone interface.

DETAILED DESCRIPTION OF THE INVENTION

Figure 1:
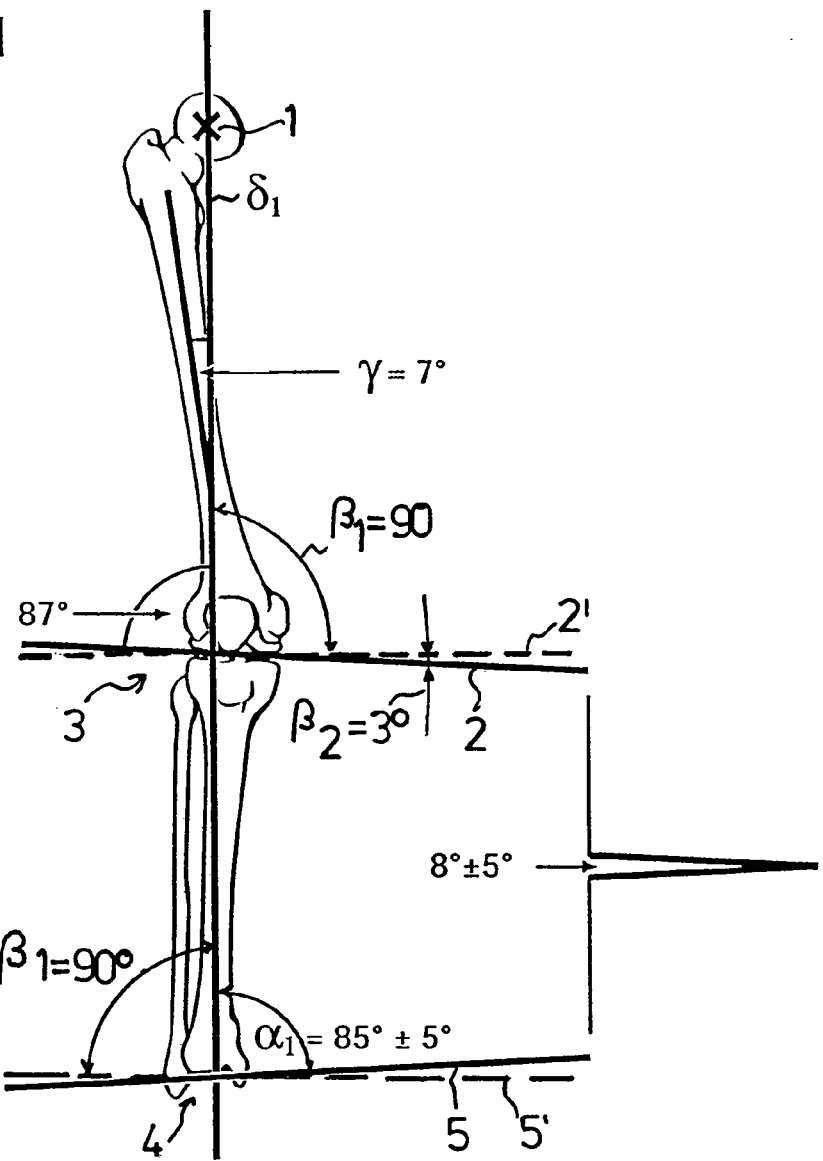
FIG. 1 is a side view of the tibia, knee joint and the femur.
Figure 2:
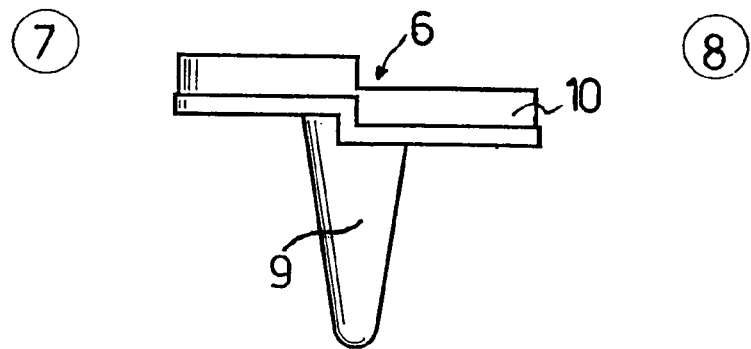
FIG. 2 is a side view of a first embodiment of a tibial implant of a knee prosthesis pursuant to the present invention.

The tibial implant shown in FIG. 2 has a stepped tibial plateau 6 that descends, due to the step which is oriented to the axis of a shaft 9, centrally from the lateral side 7 to the medial side 8. The tibial plateau 6 is formed by a layer 10 of polyethylene. The remainder of the tibial implant is made of metal.

Figure 3:
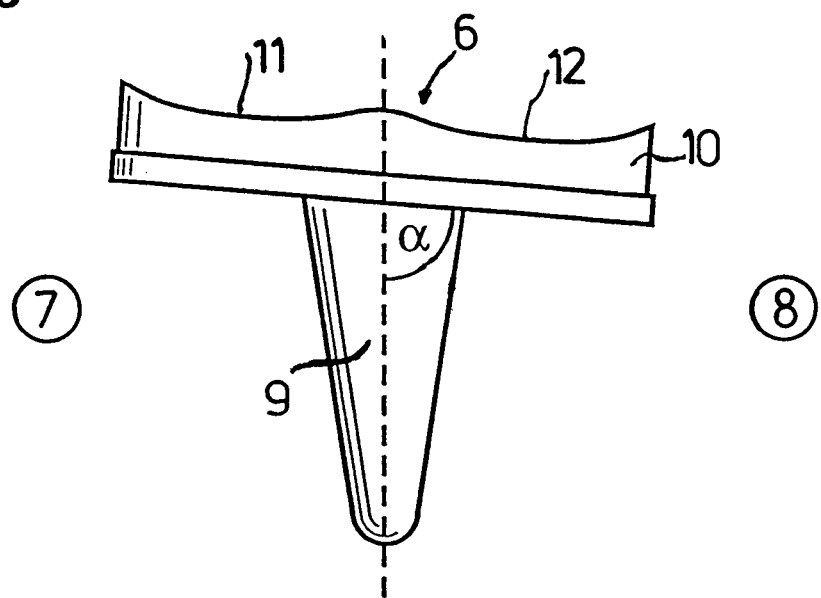
FIG. 3 is a side view of a second embodiment of a tibial implant.

The tibial implant shown in FIG. 3 has a polyethylene layer 10 that forms a tibial plateau 6 with treads 11, 12. The tibial plateau 6 is at an angle $\alpha<90°$ to the axis of the shaft 9 so that the tibial plateau 6 descends from the lateral side 7 to the medial side 8.

Figure 4:
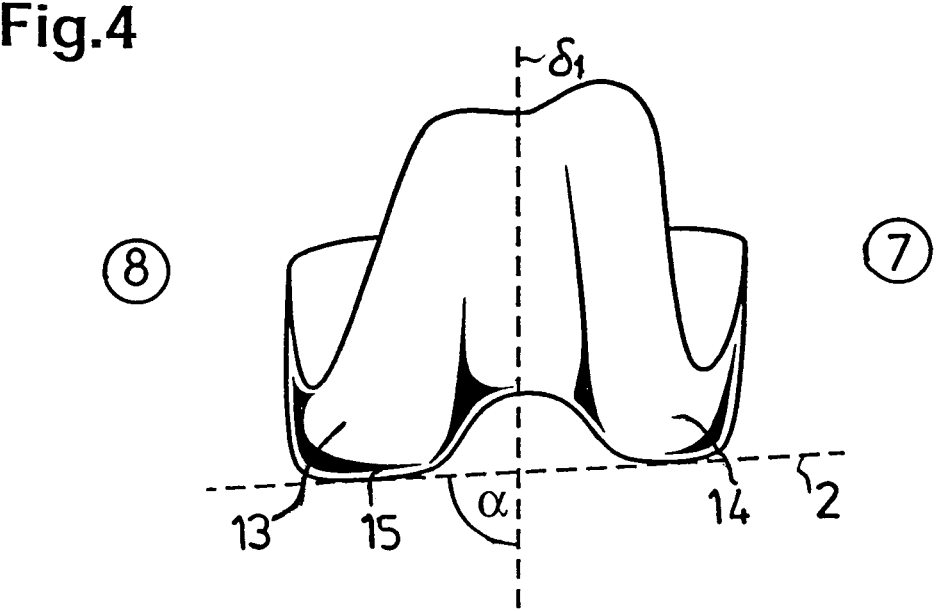
FIG. 4 is a side view of first embodiment of a femur implant of a knee prosthesis pursuant to the present invention.

The femoral implant shown in FIG. 4 has two condylar parts 13, 14, whereby the condylar part 14 is offset relative to the condylar part 13 in a proximal (towards the head) and ventral (towards the front) direction. Due to the offset the joint line 2 is at an angle $\alpha<90°$ to the mechanical axis $\delta_1$. The joint line 2 descends from the lateral side 7 to the medial side 8.

Figure 5:
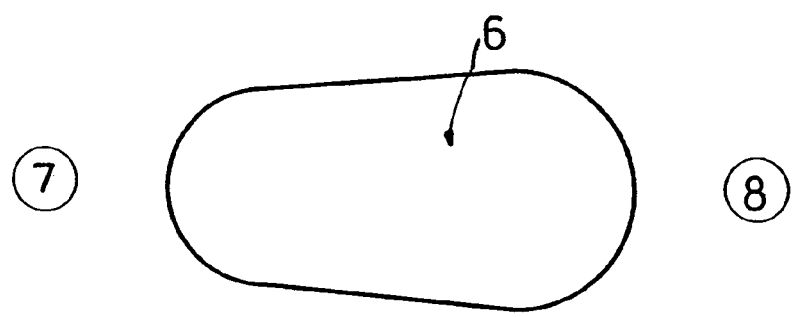
FIG. 5 is a top view of the tibial plateau of the tibial implant of FIG. 3.

The top view in FIG. 5 of the tibial implant of FIG. 3 shows that the width increases from the lateral side 7 to the medial side 8.

Figure 6:
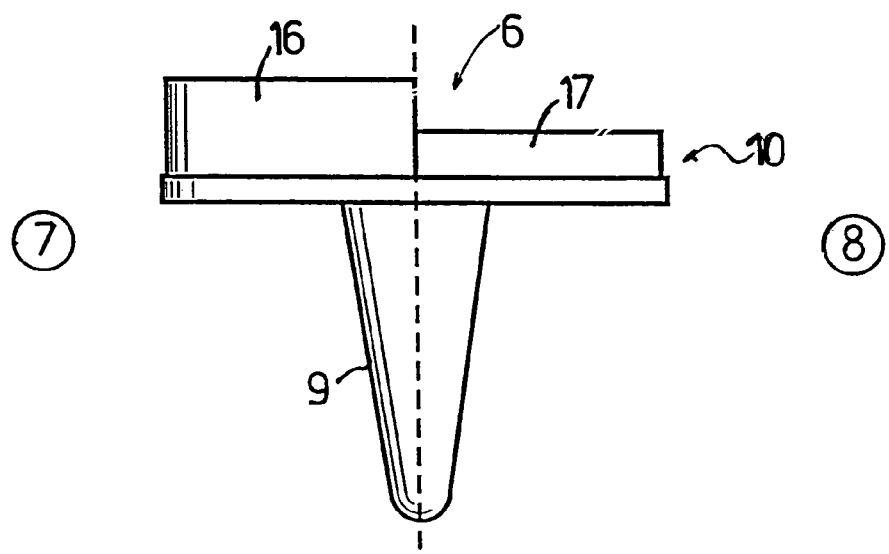
FIG. 6 is a side view of a third embodiment of a tibial implant.

The tibial implant shown in FIG. 6 has a polyethylene layer 10 that is formed by two parts 16, 17. The polyethylene part 16 on the lateral side 7 is thicker than the polyethylene part 17 on the medial side 8 so that the tibial plateau 6 in the middle is inclined to the axis of the shaft 9 and in the middle descends in the medial direction.

Figure 7:
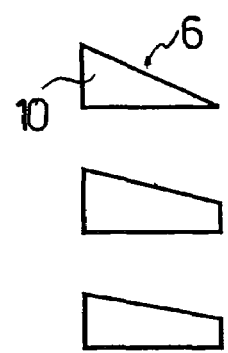
FIG. 7 is a side view of different polyethylene inlays for building a tibia plateau.

FIG. 7 shows that the layer or insert 10 can be configured to form a tibial plateau 6 that can descend in the dorsal direction at various steep angles.

Figure 8:
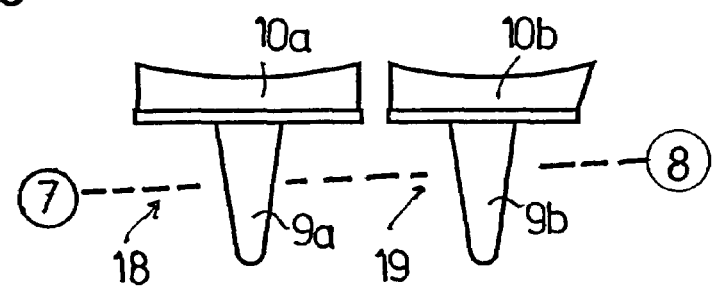
FIG. 8 shows a fourth embodiment of a tibial implant that is made of two parts.

The tibial implant shown in FIG. 8 has two parts 18, 19 each with a shaft 9a, 9b and a polyethylene layer 10a, 10b. Both parts can be implanted so that the tibial plateau formed by the two parts descends from the lateral side 7 to the medial side 8.

Figure 9:
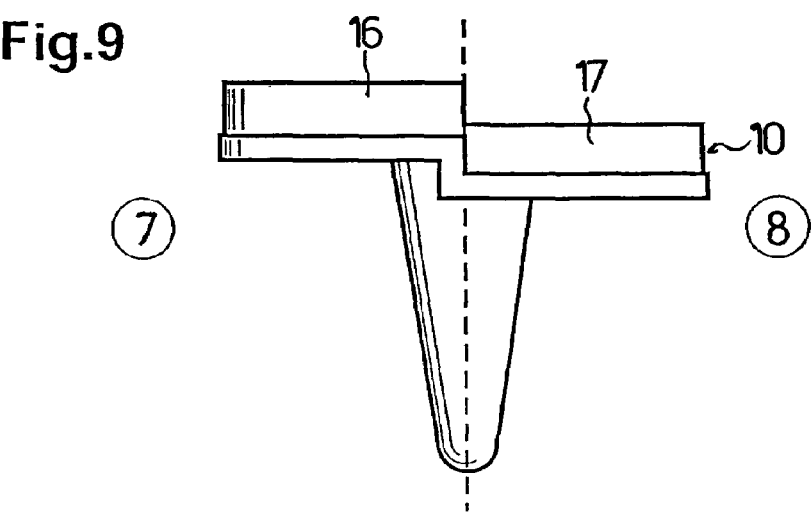
FIG. 9 is a view of a fifth embodiment of a tibial implant.

The tibial implant shown in FIG. 9 differs from the tibial implant in FIG. 2 in that the polyethylene layer 10 is not a single piece but instead is made of two pieces 16, 17 of equal thickness.

Figure 10:
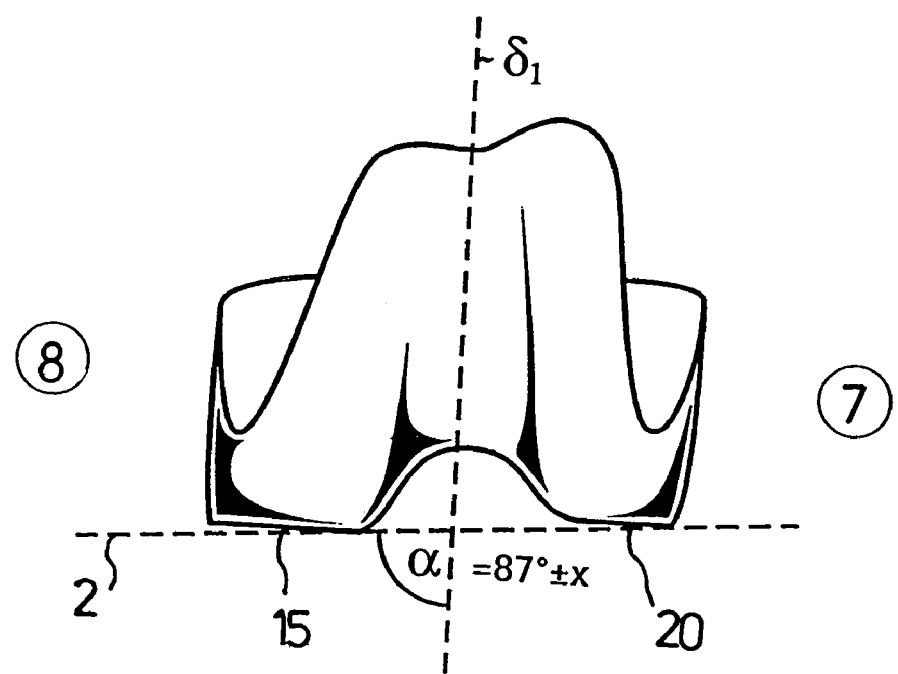
FIG. 10 is a view of a second embodiment of a femur implant.

The embodiment of a femoral implant shown in FIG. 10 differs from the embodiment shown in FIG. 4 in that the condylar running surfaces 15, 20 do not correspond to the slant of the joint line 2 in the medial direction, but instead are perpendicular to the axis $\delta_1$.

Figure 11:
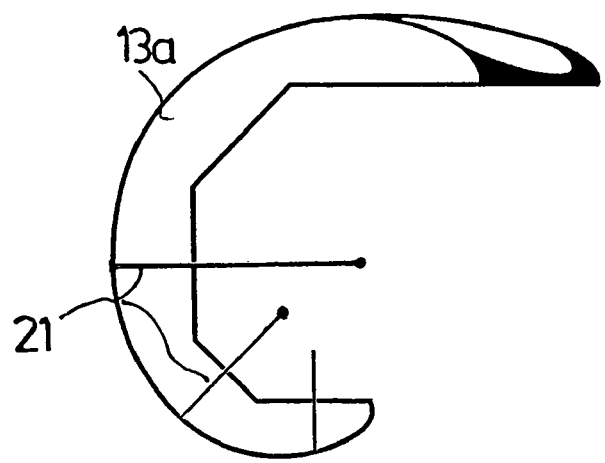
FIG. 11 shows a third embodiment of a femur implant in a lateral (a) side view and a medial (b) side view.
Figure 11:
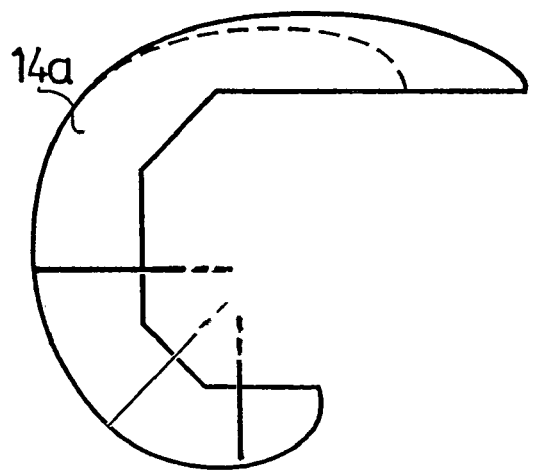

FIG. 11a shows a lateral side view in the medial direction of a femur implant. FIG. 11b is a medial side view in the opposite direction. FIG. 11a shows a lateral condylar part 13a and FIG. 11b shows a medial condylar part 14a. The condylar part 13a has smaller polycentric radii 21 than the condylar part 14a.

Figure 12:
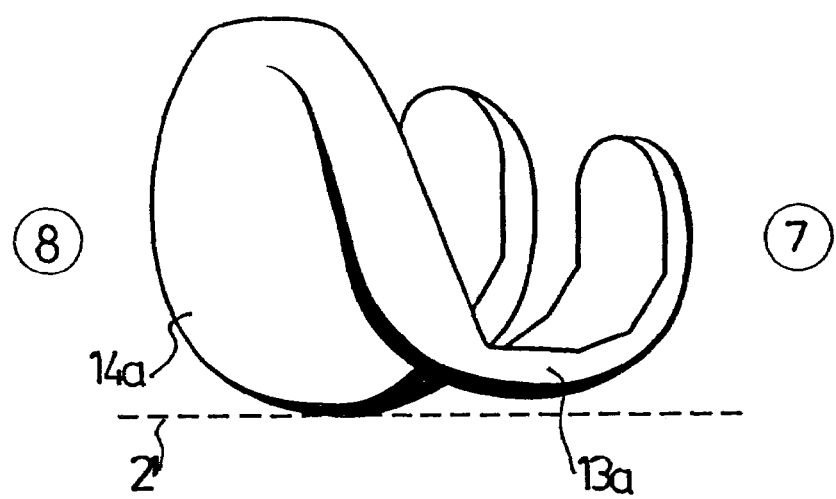
FIG. 12a shows a perspective view of a femur implant.
FIG. 12b shows a perspective view of another femur implant.
Figure 12:
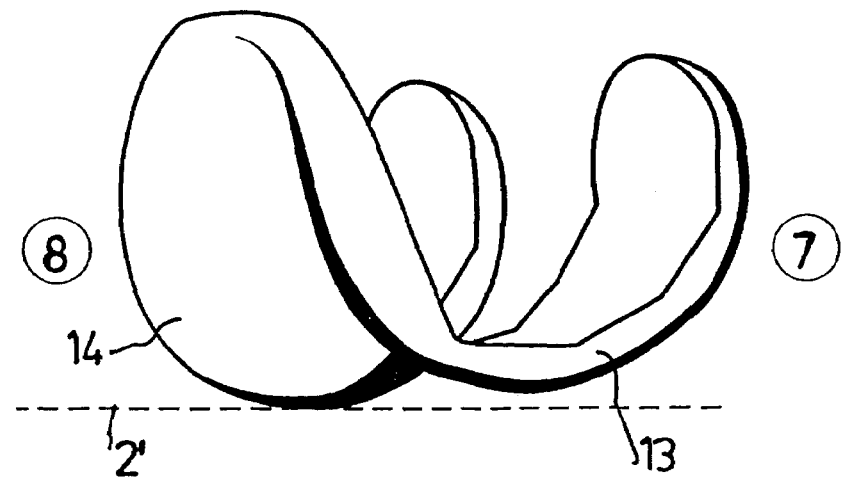
Figure 13:
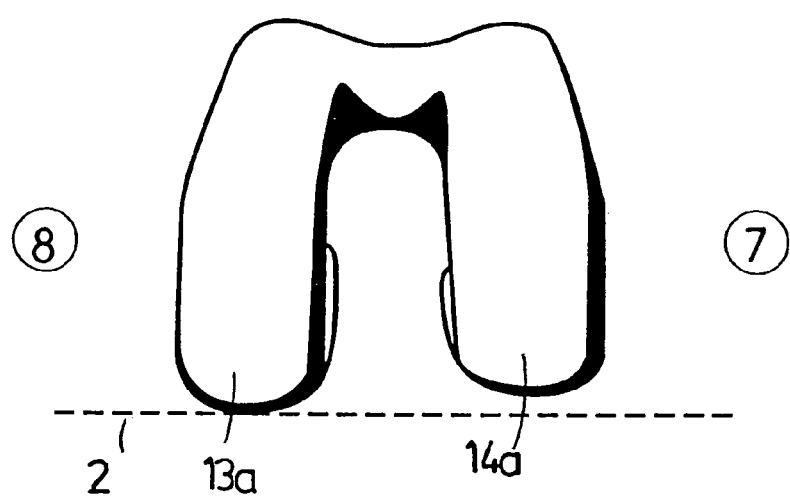
FIGS. 13a and 13b show front views of the femur implants of FIGS. 12a and 12b.
Figure 13:
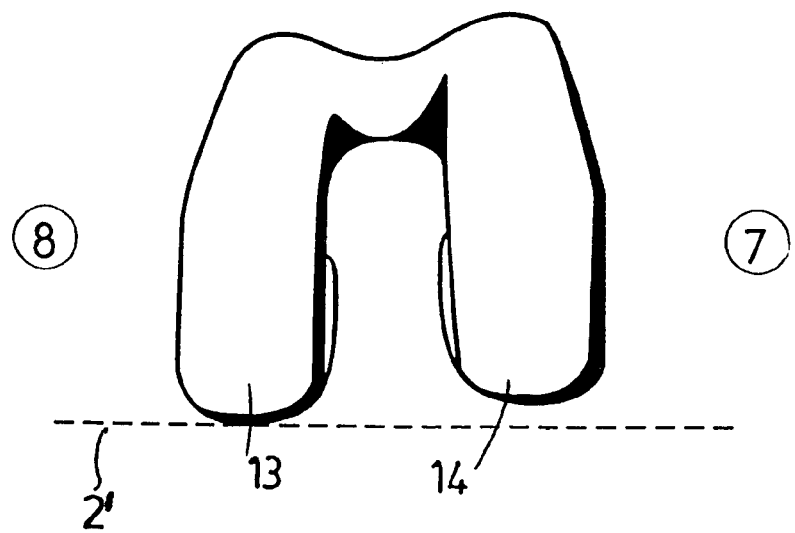

FIG. 12a is a perspective view of a femoral implant corresponding to the femoral implant of FIG. 11a. FIG. 12b is a perspective view of a femoral implant corresponding to the femoral implant of FIG. 4. FIGS. 13a and 13b show the implants of FIGS. 12a and 12b in a front view.

LIST OF REFERENCE NUMBERS

FIG. 1:

1 = mechanical axis $\delta_1$
2 = anatomical line of the interarticular space of the knee

FIG. 2:

1 = lateral
2 = medial
3 = polyethylene
4 = metal
5 = stem

FIG. 3:

1 = lateral
2 = medial
3 = angle < 90°

FIG. 4:

1 = lateral
2 = medial
3 = bearing surface = width greater medially than laterally
4 = angle < 90°

FIG. 5:

1 = lateral
2 = medial

FIG. 6:

1 = lateral
2 = medial
3 = polyethylene inlays with different heights

FIG. 8:

1 = lateral
2 = medial

FIG. 9:

1 = lateral
2 = medial

FIG. 10:

1 = lateral
2 = medial

FIG. 12 a:

1 = lateral
2 = medial

FIG. 12 b:

1 = lateral
2 = medial

FIG. 13 a:

1 = lateral
2 = medial

FIG. 13 b:

1 = lateral
2 = medial

The invention claimed is:

1. An anatomical knee prosthesis comprising a femur implant with a medial condylar part and a lateral condylar part, the condylar parts having treads dimensioned to substantially correspond to the treads of condylar parts of a healthy knee, the treads of the lateral condylar part being offset relative to the treads of medial condylar part in a proximal (towards the head) and ventral (towards the front) direction.

2. The anatomical knee prosthesis according to claim 1, further comprising a medially descending tibial implant.

3. The anatomical knee prosthesis according to claim 2, wherein the implants are configured so that, after implantation, the femur shaft and the tibia shaft form an angle of 5-7° valgus.

4. The anatomical knee prosthesis according to claim 3, wherein the bearing surface of the femoral condylar part has different widths medially and laterally.

5. The anatomical knee prosthesis according to claim 2, wherein the femur has condyles with differently sized polycentric condylar parts including a medial condylar part with a different polycentric radius from a lateral condylar part, so that, with respect to a joint bearing surface, a medially descending angle of 3°±x to the mechanical axis is achieved.

6. The anatomical knee prosthesis according to claim 5, wherein the condylar bearing surface is arranged so that the joint surface is lower (more distal) medially than laterally.

7. The anatomical knee prosthesis according to claim 6, wherein the joint surface is constructed from the lateral to the medial at an angle α to the bearing axis.

8. The anatomical knee prosthesis according to claim 6, wherein the joint surface is constructed by medial and lateral bearing surfaces with different height levels, each of which forms a 90° angle to the bearing axis.

9. The anatomical knee prosthesis according to claim 2, wherein the tibial implant has a tibial plateau anatomically implanted so as to generate a medially descending angle of 3°±x.

10. The anatomical knee prosthesis according to claim 9, wherein the tibial implant is implanted to descend dorsally by 3-10°, descend medially by 3°±x**, and, with respect to the bearing surface, more pronounced medially than laterally.

11. The anatomical knee prosthesis according to claim 2, wherein the tibial joint has a joint surface with a stepped resection, the tibial implant having a corresponding bearing surface with different height levels so as to create a medially downward sloping tibial joint surface.

12. The anatomical knee prosthesis according to claim 1, and further comprising a patellar shield.

13. The anatomical knee prosthesis according to claim 12, wherein the tibial plateau is provided with a stem, which forms an angle of 87°±x in the medial direction.

14. The anatomical knee prosthesis according to claim 12, wherein the tibial plateau has a stem fixed at right angles on the tibial plateau implant that is inserted in the bone only at a medially descending angle of 3°±x.

15. The anatomical knee prosthesis according to claim 14, wherein the tibial plateau implant is metal and a different polyethylene inlay level is set on the tibial plateau metal implant with the stem fixed at right angles so that an angle which is truer to the anatomical situation is produced by the polyethylene inlay part, which is somewhat deeper medially.

16. The anatomical knee prosthesis according to claim 15, wherein the polyethylene inlays have different dorsal slopes, so that in the case of a metallic tibial plateau component horizontally mounted in the lateral plane, the dorsal slope (tibial slope), which is usually different medially and laterally, is optimally reproduced.

17. The anatomical knee prosthesis according to claim 1, including a rotating polyethylene monoblock with different medial and lateral levels.

18. The anatomical knee prosthesis according to claim 1, wherein a tibial plateau is implanted as an unicondylar medial and lateral implant to reconstruct the anatomical downward slope in the medial and dorsal direction, so that the dorsal slope may have a different angle of slope medially and laterally.

19. The anatomical knee prosthesis according to claim 18, wherein polyethylene components are individually inserted medially and laterally, so that the joint line, as seen from medial to lateral is reproduced.

* * * * *